United States Patent [19]

Acuff

[11] 4,142,858
[45] Mar. 6, 1979

[54] METHOD TO DETERMINE A DIAGNOSTIC INDICATOR OF BLOOD SUGAR CONDITION, AND, A LIQUID CHROMATOGRAPHIC MICROCOLUMN THEREFOR

[75] Inventor: Kenneth J. Acuff, Clinton, Ohio

[73] Assignee: Isolab, Incorporated, Barberton, Ohio

[21] Appl. No.: 856,725

[22] Filed: Dec. 2, 1977

[51] Int. Cl.$^2$ .................. G01N 33/16; G01N 31/08
[52] U.S. Cl. ............................ 23/230 B; 210/31 C; 422/60; 422/68; 422/70; 422/101
[58] Field of Search .......................... 23/230 B, 259; 210/31 C

[56] References Cited
PUBLICATIONS

B. F. Horton et al., J. Chromatog., 47, 493–498 (1970).

*Primary Examiner*—Sidney Marantz
*Attorney, Agent, or Firm*—Mack D. Cook, II

[57] ABSTRACT

A method to determine a numerical percentage value as a diagnostic indicator of the blood sugar condition of a specific person. A whole blood sample is lysed and introduced into an improved ion exchange resin (Amberlite CG-50, Type II) liquid column for microchromatographic separation of hemolysates. Amounts of hemoglobin species, particularly Hb-$A_{1a\text{-}c}$, are detected and measured by spectrometric (color) analysis. A mathematical computation using integer factors corresponding to amounts of various hemoglobin species produces the numerical percentage value.

6 Claims, 1 Drawing Figure

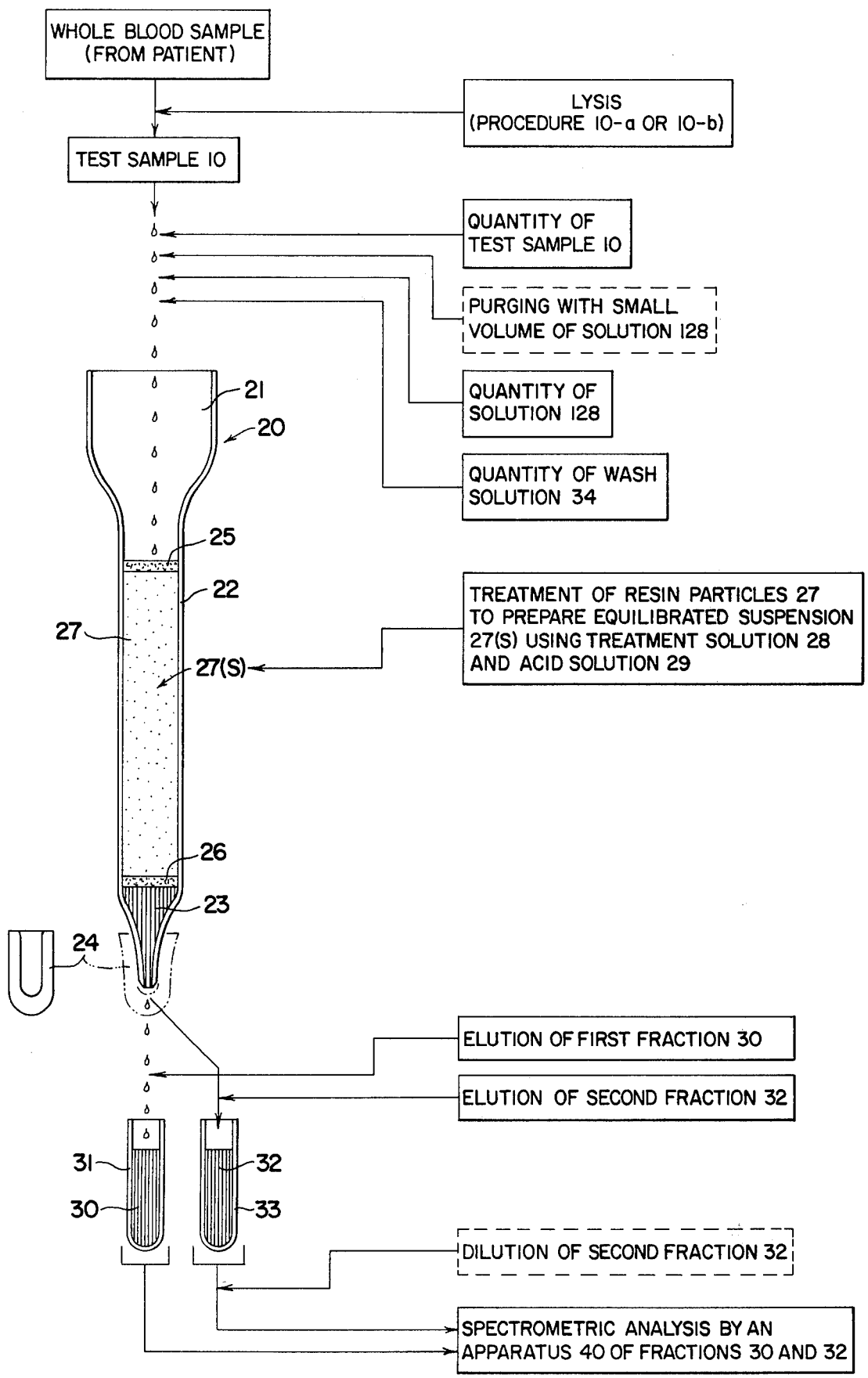

METHOD TO DETERMINE A DIAGNOSTIC INDICATOR OF BLOOD SUGAR CONDITION, AND, A LIQUID CHROMATOGRAPHIC MICROCOLUMN THEREFOR

CROSS-REFERENCE TO RELATED APPLICATIONS

This application has certain subject matter in common with simultaneously filed application Ser. Nos. 856,721; 856,722; 856,723; and 856,724.

BACKGROUND OF THE INVENTION

The invention relates to a method to determine a numerical percentage value as a diagnostic indicator of the blood sugar condition of a specific person. The invention also relates to an improved liquid chromatographic column for practice of the method.

According to the invention, a whole blood sample is collected from the person or patient and thereafter prepared as a red blood cell hemolysate test sample using alternative clinical chemistry techniques and procedures. Thereafter, the invention provides a series of steps for separating, detecting and measuring the amount of a group of hemoglobin species present in the test sample using improved ion exchange resin liquid column microchromatographic apparatus, techniques and procedures, spectrometric analysis, and mathematical computation.

In biochemistry, hemoglobins are the amphoteric protein molecule coloring matter of the red blood corpuscles serving to convey oxygen to the tissues. Several chromatographically separable minor hemoglobins are present in red blood cell hemolysates of normal persons. Some minor hemoglobins are designated as $Hb-A_{1a}$, $Hb-A_{1b}$, $Hb-A_{1c}$, $Hb-A_{1d}$, and $Hb-A_{1e}$. The hemoglobin species $Hb-A_{1c}$ is most prominent and accounts for the major portion of the minor hemoglobins. It is known that the level of hemoglobin $Hb-A_{1c}$ has been related to a patient's average blood sugar level. Normal persons are expected to have 3-6% $Hb-A_{1c}$ relative to their total hemoglobin. Untreated diabetics may have 6-12% $Hb-A_{1c}$ relative to their total hemoglobin, whether the affliction is of the juvenile-onset or adult-onset type. Still further, it is understood that the levels of the species $Hb-A_{1a-c}$, as a separate and identifiable sub-group, may serve as an indicator of the degree of hyperglycemia, an excess of sugar in the blood, over a prolonged period of time.

Prior literature relating to the diagnosis of abnormal blood sugar (diabetes mellitus) by determination and measurement of the level of the hemoglobin species $Hb-A_{1c}$ includes: (i) The Relation Between the Minor Components of Whole Normal Human Adult Hemoglobin as Isolated by Chromatography and Starch Block Electrophoresis, Schnek and Schroeder, *Journal of the American Chemical Society*, Vol. 83, pp. 1472-1478, March 1961; (ii) Hemoglobin Components in Patients with Diabetes Mellitus, Trivelli, et al., *New England Journal of Medicine*, Vol. 84, pp. 353-357, February 1971; (iii) The Biosynthesis of Human Hemoglobin $A_{1c}$, Bunn, et al., *Journal of Clinical Investigation*, Vol. 57, pp. 1652-1659, June 1976; (iv) Correlation of Glucose Regulation And Hemoglobin $A_{1c}$ in Diabetes Mellitus, Koenig, et al., *New England Journal of Medicine*, Vol. 295, pp. 417-420, August 1976; (v) Red Cell Age-Related Changes of Hemoglobins $A_{1a+b}$ and $A_{1c}$ in Normal and Diabetic Subjects, Fitzgibbons, et al., *Journal of Clinical Investigation*, Vol. 58, pp. 820-824, October 1976; (vi) Glycosylated Hemoglobins and Long-Term Blood Glucose Control in Diabetes Mellitus, Gabbay, et al., *Journal of Clinical Endocrinology and Metabolism*, Vol. 44, pp. 859-864, 1977; and, (vii) Rapid Estimation (2½ Hours) of Glycosylated Hemoglobin For Routine Purposes, Kynoch and Lehmann, *The Lancet*, p. 16, July 1977.

Until now, the clinical techniques and procedures for determination of the level of the hemoglobin species $Hb-A_{1c}$ have had the disadvantage of requiring elaborate equipment and a testing time space of several hours or even days. It has now been found possible, according to the invention, to determine, as a numerical percentage value, the ratio of the sub-group of hemoglobin species $Hb-A_{1a-c}$ to the total hemoglobins (Hb) quickly, inexpensively and accurately. Such a numerical percentage value is available for use as a diagnostic indicator of the blood sugar characteristics of the suspected diabetic.

SUMMARY OF THE INVENTION

It is an object of the invention to provide a method to determine a numerical percentage value as a diagnostic indicator of the blood sugar condition of a specific person.

It is a further object to provide a method which will separate, detect and measure the ratio of the sub-group of hemoglobin species $Hb-A_{1a-c}$ to the total hemoglobins (Hb) present in the blood of a specific person quickly, inexpensively and accurately.

It is still further an object to provide a method which, although requiring of a number of sequential or consecutive steps, is of such a character and nature as to permit the adoption of procedures and protocols which may become standard and routine, permitting persons skilled in the art of clinical chemistry to repeatedly and accurately test the blood of large groups of persons to establish a data base for use by qualified, specialized and medically trained personnel in diagnosing the blood sugar condition of specific persons suspected as being diabetic.

It is still another object of the invention to provide a series of identical ion exchange resin liquid columns having predetermined microchromatographic characteristics and properties for practice of the method according to the invention.

These and other objects of the invention, as well as the advantages thereof, will be apparent in view of the detailed descriptions of the various embodiments thereof as set forth below.

In general, the method according to the invention uses a whole blood sample taken from a person or patient and thereafter prepared as a test sample containing a red blood cell hemolysate solution. Thereafter, a quantity of the test sample is introduced into an end of a column bed of ion exchange resin particles. The column bed comprises a suspension of particles of a copolymer of methacrylic acid and divinylbenzene containing negatively charged functional carboxyl groups and having a 200-400 mesh size and an equilibrated pH of substantially 6.8 at 22.5° C. which will adsorb the blood components of the test sample. Then, a quantity of 2-hydroxyethyl ("bis")-trihydroxy-imino-methane ("tris")-cyanide-chloride solution is introduced into an end of the column bed to elute therefrom a fraction of the test sample, which is understood as being predominately $Hb-A_{1a-c}$. Thereafter, an aliquot quantity of a first eluate fraction is collected from the other end of the column bed.

In the first embodiment of the invention, a quantity of a wash solution is then introduced into an end of the column bed to desorb substantially all the remaining blood components of the test sample from the resin particles. Thereafter, an aliquot quantity of a second eluate fraction is collected from the other end of the column bed.

Then, the hemoglobin species present in each of the eluate fractions are separately detected and measured by spectrometric analysis with the respective amounts thereof being expressed as an integer. Thereafter, the amount of hemoglobin species in the first eluate fraction is compared to the sum of the amounts of hemoglobin species in the first and second fractions, according to the mathematical formula $$\frac{\text{integer for first eluate fraction} \times 100}{\text{integer for first eluate fraction} + \text{integer for second eluate fraction}} =$$

a numerical percentage value.

In the second embodiment of the invention, the first fraction is eluted from the column bed of resin particles. Also, a quantity of a test sample is significantly diluted to provide a red blood cell hemolysate fraction which may be conveniently detected and measured by spectrometric analysis. Then, the hemoglobin species present in the first eluate fraction and the hemolysate fraction are separately detected and measured by spectrometric analysis with the respective amounts thereof being expressed as an integer. Thereafter, the amount of hemoglobin species in the first eluate fraction is compared to the amount of hemoglobin species in the hemolysate fraction according to the mathematical formula $$\frac{\text{integer for first eluate fraction} \times 100}{\text{integer for hemolysate fraction}} =$$

a numerical percentage value.

In both embodiments of the invention, the resultant numerical percentage value is available for use by qualified, specialized and medically trained personnel as a diagnostic indicator of the blood sugar characteristics of the patient providing the test sample.

A microcolumn for use in the practice of either embodiment of the invention has a reservoir discharging into a barrel terminating in a discharge tip. The junctures between the reservoir and barrel and the barrel and discharge tip are closed by transverse discs. Ion exchange resin particles positioned in the barrel between the discs provide a column bed. The discs are permeable to a red blood cell hemolysate solution. The column bed comprises the suspension of particles of a copolymer of methacrylic acid and divinylbenzene containing negatively charged functional carboxyl groups and having a 200-400 mesh size and an equilibrated pH of substantially 6.8 at 22.5° C. Preferably, the suspension of particles is prepared by converting the resin particles to a sodium form which is then treated with a 2-hydroxyethyl ("bis")-trihydroxy-imino-methane ("tris")-cyanide solution. The treated sodium form is further treated with an acid solution. The treatment with the bis-tris-cyanide and acid solutions is repeated until the suspension has the stated equilibtated pH.

THE DRAWING

The drawing schematically shows practice of the invention specifically as to the first embodiment wherein first and second fractions of hemoglobin species are eluted from an improved chromatographic microcolumn shown substantially in full scale.

DETAILED DESCRIPTION OF THE INVENTION

Practice of the method according to the invention requires the collection of a whole blood sample from a person or patient. The whole blood sample may be taken using conventional clinical chemistry techniques and procedures.

There are at least two procedures for preparing a suitable test sample, referred to generally by the numeral 10, containing a red blood cell hemolysate solution from a whole blood sample. Procedure 10-a is used to prepare a test sample 10 which is predominately the hemoglobin content of the whole blood sample. Procedure 10-b is used to prepare a test sample 10 which may include the plasma proteins, lipids, and the white and red blood cell debris, in addition to the hemoglobin content of the whole blood sample.

A 10-a procedure may include centrifuging the red blood cells from a whole blood sample which has been treated with a conventional anti-coagulant such as EDTA (Ethylenediaminetetraacetic Acid). After decanting the supernate, the precipitate in the centrifuge tube must be thoroughly washed using a physiological saline solution. Preferably, the washing procedure is repeated three times using a 0.85% NaCl solution and centrifugation. The washed precipitate is then lysed, as by vigorous mixing with a preferably equal volume of distilled water for approximately two minutes. The resultant lysate is predominately a hemolysate although containing small amounts of other proteins, lipids and cell membrane remnants. The lysate may be further treated by mixing with a solvent. Preferably, a 0.2 volume of $CCl_4$ (carbon tetrachloride) is vigorously mixed with one volume of the lysate, then set aside for thirty minutes at room temperature, and again finally centrifuged. The resultant supernate (after dilution) is the test sample 10 of a red blood cell hemolysate solution for separation, detection and measurement of the amount of a group of hemoglobin species present, according to the invention.

A 10-b procedure will include collecting a relatively small volume whole blood sample as by use of a microhematocrit tube. One volume of a whole blood sample is mixed with four volumes of water. Preferably, one drop of whole blood and four drops of distilled water are vigorously shaken together in a small test tube. Then, the test tube is set aside for five minutes at room temperature. After another and final mixing, the resultant suspension (without dilution) includes a test sample 10 of a red blood cell hemolysate solution for separation, detection and measurement of the amount of a group of hemoglobin species present, according to the invention.

It is to be understood that the procedure 10-b, as described above, is considerably less complex and less expensive than procedure 10-a. It has been found that the subsequent steps required for practice of the method according to the invention are of such character and nature as to provide for the separation, detection and measurement of the amount of a group of hemoglobin species present in the blood of the person or patient, even though other blood components present in the test sample might, at least in theory, obscure or interfere with the intended measurement.

Practice of the method according to the invention next requires the use of a liquid microchromatographic column comprising particles of an ion exchange resin. Such columns for use in clinical chemistry techniques and procedures are not new and are conventional. However, as shown in the drawing by the full scale view, the chromatographic microcolumns used in the practice of the invention are significantly smaller than ion exchange resin columns as used in industrial or chemical processes or procedures, or as heretofore used in microchromatographic column techniques for determining the presence of hemoglobin species as blood components.

With reference to the drawing, a chromatographic microcolumn is indicated generally by the numeral 20. A column 20 comprises a reservoir 21 discharging into a barrel 22 terminating in a discharge tip 23 selectively closed by a cap 24. The juncture or intersection between the reservoir 21 and the barrel 22 is closed by a transverse plate or disc 25. The juncture between the barrel 22 and the discharge tip 23 is also closed by a transverse plate or disc 26. The ion exchange resin particles comprising the column bed between the discs 25 and 26 are referred to generally by the numeral 27.

Each retaining disc 25 and 26 is permeable, having a network of micropores permitting introduction of a red blood cell hemolysate solution from reservoir 21 into the barrel 22, and removal of an eluate fraction from the barrel 22 through the tip 23, while retaining the column bed of resin particles 27 and adsorbents thereon within the barrel 22. The discs 25 and 26 may be made from a conventional flexible, resilient, linear, high density polyethylene of the Ziegler type. Commercially, this type of filter grade polyethylene is produced and sold under the name Vyon.

According to the invention, the resin particles 27 are of a weak and cation exchange type. More specifically, the resin is a 200–400 mesh fraction, carefully screened to eliminate other larger or smaller size particles, of a conventional copolymer of methacrylic acid and divinylbenzene, containing negatively charged carboxyl groups. Commercially, this type of resin is produced and sold under the name Amberlite CG-50, Type II.

The commercially available form of ion exchange resin particles 27 must be prepared or treated for use in the barrel 22 of the microcolumn 20 between the discs 25 and 26. Such treatment could be performed with the resin particles 27 in situ in the column barrel 22. However, it is preferred that the resin particles 27 for a series of identical columns 20 be treated using a batch technique, which will permit the use of columns 20 having predetermined microchromatographic characteristics and properties.

The resin particles 27 are used in the barrel 22 of the column 20 in the form of an equilibrated suspension, referred to generally by the numeral 27(S), and having a predetermined or "starting" pH. The suspension 27(S) may be prepared by placing a reasonable quantity of particles 27 in a treatment container of suitable size. The particles are first converted to a sodium form, displacing $H+$ ions thereon, by thorough mixing with an excess quantity of sodium hydroxide (e.g., 1 N NaOH). The excess NaOH solution and any remaining unscreened or fine resin particles are removed by repeated washings with distilled water. The sodium form of resin particles 27 is suspended and equilibrated to a pH of substantially 6.8 at 22.5° C. by treatment and thorough mixing with a bis-tris-cyanide treatment solution referred to generally by the numeral 28.

The resin treatment solution 28 may be of the formula: 6.28g $(HOCH_2CH_2)_2NC(CH_2OH)_3$ (0.03M) and 0.10g KCN (0.01%), with 0.10g $NaN_3$ (0.01%) as a preservative, made up in one liter of $H_2O$. Thereafter, the pH of solution 28 is adjusted to substantially 6.8 at 22.5° C. using concentrated HCl. After mixing with the treatment solution 28, the sodium form of the resin particles 27 is then further treated with an acid solution 29 (e.g., 4 M HCl), to adjust to a pH of substantially 6.8 at 22.5° C. The treatments with the solution 28 and the acid solution 29 should be repeated a sufficient number of times to obtain a suspension 27(S) which is equilibrated and at the desired pH. Thereafter, the barrel 22 of one or more microcolumn 20 is filled with the resin particle suspension 27(S) being positioned or held in place by the permeable discs 25 and 26.

A quantity of a test sample 10 prepared by either procedure 10-a or 10-b is introduced into one end of a column 20 having a column bed comprising an equilibrated suspension 27(S) of resin particles 27. A test sample prepared according to procedure 10-a will require a 1:4 dilution using distilled water.

Preferably, the column 20 is positioned vertically, the discharge tip cap 24 is removed and a predetermined quantity or volume of a test sample 10 is discharged or placed into the reservoir 21. A major portion of the test sample 10 will pass readily through the disc 25 and onto the column bed of resin particles 27. The minor portion of the test sample 10 remaining on or in the disc 25 should be purged or displaced onto the column bed of resin particles 27, using a small volume (e.g., 0.2 ml) of an elution solution 128 discharged or placed into the reservoir 21. The solution 128 will rapidly pass through the disc 25 and onto the column bed of resin particles 27, carrying with it the last portion of the test sample 10.

The elution solution 128 may be of the formula: 6.28g $(HOCH_2CH_2)_2NC(CH_2OH)_3$ (0.03M), 0.10g KCN (0.01%) and 7.02g NaCl (0.12M), with 0.10g $NaN_3$ (0.01%) as a preservative, made up in one liter of $H_2O$. Thereafter, the pH of the bis-tris-cyanide-chloride solution 128 is adjusted to substantially 6.8 at 22.5° C. using concentrated HCl.

The next step according to the invention is the elution from the column bed of resin particles 27 of a fraction of a test sample 10, which is understood as being predominantly Hb-$A_{1a-c}$. The first eluate fraction, referred to generally by the numeral 30, is collected in a receiver 31 positioned adjacent the column discharge tip 23 following introduction into the column reservoir 21 of a predetermined or aliquot quantity of the bis-tris-cyanide-chloride solution 128. For example, a five milliliter (5 ml) volume of a solution 128 is discharged or placed into the reservoir 21. After a period of time (e.g., 20–30 minutes), the eluate fraction 30 of substantially 5 ml volume will be in the receiver 31. The volume of first eluate fraction 30 in receiver 31 is ready for performance of the subsequent steps according to the invention.

FIRST EMBODIMENT

In the first embodiment of the invention, the next step is the further elution from the column bed of resin particles 27 of substantially all the remaining blood components of the test sample 10. This second eluate fraction, referred to generally by the numeral 32, is collected in a receiver 33 from the column tip 23, following introduction into the column reservoir 21 of a preferably predetermined or aliquot quantity of a "wash" or complete desorption solution referred to generally by the numeral 34.

The precise formula of a wash solution 34 is not critical, so long as use thereof will not alter or modify the spectrometric absorption characteristics ("color") of an eluate fraction 32. A compatible wash solution 34 will have either an ionic strength or relative pH sufficient to fully or completely desorb substantially all the remaining blood components of the test sample 10 from the column bed of resin particles 27. For example, a four milliliter (4 ml) volume of 4M NaCl may be discharged or placed into the column reservoir 21. After a period of time (e.g., 20–30 minutes), an eluate fraction 32 of susbstantially 4 ml volume will be collected in the receiver 33. The volume of the eluate fraction 32 in receiver 33 will require of suitable dilution using distilled water prior to performance of the subsequent steps according to the invention.

According to both embodiments of the invention, the amount of Hb-$A_{1a-c}$ present in the whole blood sample collected from the person or patient is detected and measured using spectrometric apparatus referred to generally by the numeral 40, following performance of liquid column microchromatographic techniques and procedures using a test sample 10.

The spectrometric analysis is performed by an apparatus 40 which measures absorption of light caused by the hemoglobin species present in the test sample 10. It is known that the visible portion of the spectrum for detecting the presence of a hemoglobin is in the violet range, more specifically, at substantially 415 nm or 4150 A.

The apparatus 40 may be an optical spectrometer "dedicated" or pre-set at the selected wave length of 415 nm. The apparatus 40 may also be a spectrophotometer, a form of spectrometer with associated equipment which supplies the ratio, or a function of the ratio, of the radiant power of two beams as a function of an adjustably selected spectral wave length. Because the spectrometric analysis according to the invention is for the purpose of detecting and measuring hemoglobin species from the test sample 10 by light absorption characteristics, alternative forms of apparatus 40 could be used; for example, visual comparators such as a set of Nessler tubes.

In the first embodiment, the contents of the receivers 31 and 33 are individually transferred into appropriate cuvettes for the spectrometric apparatus 40. It has been found that the light absorption characteristics of the second eluate fraction 32 are of such a magnitude as to require dilution of the fraction for optimum operational efficiency of the sensing photocell of a conventional spectrometer or spectrophotometer. For example, a 4 ml volume of eluate fraction 32 will require a 1:5 dilution using distilled water.

Spectrometric analysis of the first and second eluate fractions 30 and 32 will provide integers or natural numbers which will express, represent or indicate the amounts of hemoglobin species present in the test sample 10. When using a conventional spectrometer or spectrophotometer as the apparatus 40, the displayed integer is a function of the absorbance (A), a measurement of the amount of light of the spectral wave length of 415 nm absorbed by the hemoglobin species during passage through the cuvette and toward the sensing photocell.

When the apparatus 40 comprises Nessler tubes, a series of standard solutions is prepared in a set of tubes, for example, of 50- or 100-ml capacity. The color of each tube in the series is assigned an arbitrary integer relating to presence of hemoglobin. The eluate fractions 30 and 32 are transferred to duplicate tubes, suitably diluted as required, and visually matched or compared with the tubes of standard solutions. When the color is matched, the eluate fractions have the same relative concentration as two tubes of the standard solutions.

The integers expressing the amounts of hemoglobin species present in each eluate fraction 30 and 32 as detected and measured by analysis in the spectrometric apparatus 40 are then used as factors in a computation. More specifically, the amount of hemoglobin species in the first eluate fraction 30 is compared to the sum of the amounts of hemoglobin species in both fractions 30 and 32, according to the mathematical formula $$\frac{\text{integer for eluate fraction 30} \times 100}{\text{integer for eluate fraction 30} + \text{integer for eluate fraction 32}} =$$

a numerical percentage value.

SECOND EMBODIMENT

As a second embodiment of the invention, the invention may be practiced using a first fraction 30 from a test sample 10, eluted from the column bed of resin particles 27. The amount of hemoglobin species in eluate fraction 30 is compared with the amount of hemoglobin species present in a quantity of a test sample 10 containing a red blood cell hemolysate fraction, referred to generally by the numeral 42.

In this embodiment, a test sample 10 of whole blood from the person or patient is prepared, as by procedures 10-a or 10-b. A quantity of test sample 10 is introduced into an end of a column 20 having a column bed comprising an equilibrated suspension 27(S) of resin particles 27. An aliquot quantity of a first eluate fraction 30 is eluted from the column 20 by a quantity of the bis-tris-cyanide-chloride solution 128 and collected in a receiver 31.

Also, either at a prior time, concurrently or consecutively, a quantity of test sample 10 is prepared as a hemolysate fraction 42 which may be conveniently analyzed by a spectrometric apparatus 40. It will be apparent that the light absorption characteristics of the test sample 10, without significant dilution, would be of such magnitude as to impair operational efficiency of the sensing photocell of conventional spectrometric apparatus 40. Accordingly, and by way of example, a quantity of test sample 10 equal to the volume of test sample 10 introduced into an end of a column 20, prior to elution of the first fraction 30, should be diluted using distilled water in the ratio substantially 1:480 to prepare a hemolysate fraction 42 for analysis by a spectrometric apparatus 40.

After individual analysis of the eluate fraction 30 and the hemolysate fraction 42, by detection and measurement in the spectrometric apparatus 40, the integers expressing the amounts of hemoglobin species present in each fraction are then used as factors in a computation. More specifically, the amount of hemoglobin species in the first eluate fraction 30 is compared to the amount of hemoglobin species in the hemolysate fraction 42 according to the mathematical formula $$\frac{\text{integer for eluate fraction 30} \times 100}{\text{integer for hemolysate fraction 42}} =$$

a numerical percentage value.

SUMMARY

In the two embodiments of the invention as described, several steps, techniques or procedures are disclosed wherein dilution, using distilled water, is either required or suggested. It will be understood by a person skilled in the art of clinical chemistry that the best modes of practicing the invention using an improved microcolumn 20 will require careful adoption and consistent following of routine procedures, if the invention is to represent a reliable method of assessing the presence of diabetes and monitoring the degree of diabetic control. It will be further understood by a practitioner of the invention that a procedure or protocol for repetitive testing of large numbers of persons, both diabetic and normal, will inherently incorporate therein: standard quantities and volumes of test samples 10, solutions 28 and 128, 29 and 34, and fractions 30, 32 or 42; consistent and compatible dilution ratios; and, careful selection and regulation of the spectrometric apparatus 40. Therefore, the full scope and extent of the invention should be determined solely by the words of the claims appended hereto.

What is claimed is:

1. A method to determine a numerical percentage value as a diagnostic indicator of the blood sugar condition of a specific person, wherein a whole blood sample is taken from said person and thereafter prepared as a test sample containing a red blood cell hemolysate solution, and thereafter, a quantity of said test sample is introduced into an end of a column bed of ion exchange resin particles, said column bed comprising a suspension of particles of a copolymer of methacrylic acid and divinylbenzene containing negatively charged carboxyl groups and having a 200–400 mesh size and an equilibrated pH of substantially 6.8 at 22.5° C. which will adsorb the blood components of said test sample, and then, a quantity of a bis-tris-cyanide-chloride solution is introduced into an end of said column red to elute therefrom a fraction of said test sample and thereafter, an aliquot quantity of a first eluate fraction is collected from the other end of said column bed, and then, a quantity of wash solution is introduced into an end of said column bed to desorb substantially all the remaining blood components of said test sample from said resin particles, and thereafter, an aliquot quantity of a second eluate fraction is collected from the other end of said column bed, and then, the hemoglobin species present in each said eluate fraction are separately detected and measured by spectrometric analysis with the respective amounts thereof being expressed as an integer, and thereafter, the amount of hemoglobin species in said first eluate fraction is compared to the sum of the amounts of hemoglobin species in each fraction, according to the mathematical formula $$\frac{\text{integer for first eluate fraction} \times 100}{\text{integer for first eluate fraction} + \text{integer for second eluate fraction}} =$$

a numerical percentage value, said numerical percentage value being a diagnostic indicator of the blood sugar characteristics of said specific person.

2. A method according to claim 1 wherein said suspension of particles is prepared by converting said resin particles to a sodium form and then treating said sodium form with a bis-tris-cyanide solution, said treated sodium form being further treated with an acid solution, said treatments with said bis-tris-cyanide solution and said acid solution being repeated until said suspension has said equilibrated pH.

3. A method to determine a numerical percentage value as a diagnostic indicator of the blood sugar condition of a specific person, wherein a whole blood sample is taken from said person and thereafter prepared as a test sample containing red blood cell hemolysate solution, and thereafter, a quantity of said test sample is introduced into an end of a colum bed of ion exchange resin particles, said column bed comprising a suspension of particles of a copolymer of methacrylic acid and divinylbenzene containing negatively charged carboxyl groups and having a 200–400 mesh size and an equilibrated pH of substantially 6.8 at 22.5° C. which will adsorb the blood components of said test sample, and then, a quantity of a bis-tris-cyanide-chloride solution is introduced into an end of said column bed to elute therefrom a fraction of said test sample and thereafter, an aliquot quantity of a first eluate fraction is collected from the other end of said column bed, also, a quantity of said test sample is significantly diluted to provide a red blood cell hemolysate fraction which may be conveniently detected by spectrometric analysis; and then, the hemoglobin species present in said first eluate fraction and said hemolysate fraction are separately detected and measured by spectrometric analysis with the respective amounts thereof being expressed as an integer, and thereafter, the amount of hemoglobin species in said first eluate fraction is compared to the amount of hemoglobin species in said hemolysate fraction according to the mathematical formula $$\frac{\text{integer for first eluate fraction} \times 100}{\text{integer for hemolysate fraction}} =$$

a numerical percentage value, said numerical percentage value being a diagnostic indicator of the blood sugar characteristics of said specific person.

4. A method according to claim 3 wherein said suspension of particles is prepared by converting said resin particles to a sodium form and then treating said sodium form with a bis-tris-cyanide solution, said treated sodium form being further treated with an acid solution, said treatments with said bis-tris-cyanide solution and said acid solution being repeated until said suspension has said equilibrated pH.

5. A microcolumn for use in the determination of a numerical percentage value as a diagnostic indicator of the blood sugar condition of a person providing a whole blood sample: having a reservoir discharging into a barrel terminating in a discharge tip, the juncture between said reservoir and said barrel and the juncture between said barrel and said tip each being closed by a transverse disc, and ion exchange resin particles positioned in said barrel between said transverse discs to provide a column bed, said discs being permeable to a red blood cell hemolysate solution prepared from said whole blood sample; said column bed comprising a suspension of particles of a copolymer of methacrylic acid and divinylbenzene containing negatively charged carboxyl groups and having a 200–400 mesh size and an equilibrated pH of substantially 6.8 at 22.5° C.

6. A microcolumn according to claim 5 wherein said suspension of particles is prepared by converting said resin particles to a sodium form and then treating said sodium form with a bis-tris-cyanide solution, said treated sodium form being further treated with an acid solution, said treatments with said bis-tris-cyanide solution and said acid solution being repeated until said suspension has said equilibrated pH.

* * * * *

UNITED STATES PATENT OFFICE
CERTIFICATE OF CORRECTION

Patent No. 4,142,858   Dated March 6, 1979

Inventor(s) Kenneth J. Acuff

It is certified that error appears in the above-identified patent and that said Letters Patent are hereby corrected as shown below:

Col. 7, line 18, "susbantially" should read -- substantially --;

Col. 7, line 37, "A" should read -- $\overset{\circ}{A}$ --;

Col. 9, line 48, "column red" should read -- column bed --;

Col. 10, line 27, "colum" should read -- column --.

Signed and Sealed this

Sixth Day of November 1979

[SEAL]

Attest:

RUTH C. MASON
Attesting Officer

LUTRELLE F. PARKER
Acting Commissioner of Patents and Trademarks